United States Patent [19]
Larsson

[11] Patent Number: 5,549,548
[45] Date of Patent: Aug. 27, 1996

[54] PROCEDURE AND DEVICE FOR FLUSHING A CATHETER

[75] Inventor: Rolf Larsson, Varby, Sweden

[73] Assignee: Siemens Elema AB, Solna, Sweden

[21] Appl. No.: 255,992

[22] Filed: Jun. 8, 1994

[30] Foreign Application Priority Data

Jun. 22, 1993 [SE] Sweden ................... 9302157

[51] Int. Cl.⁶ .................................................. A61M 1/00
[52] U.S. Cl. ............................................................. 604/35
[58] Field of Search ............................... 604/35, 30, 34, 604/49, 52, 53, 54, 246–249, 264, 280

[56] References Cited

U.S. PATENT DOCUMENTS

| | | | |
|---|---|---|---|
| 3,583,404 | 6/1971 | McWhorter | 604/43 |
| 3,929,126 | 12/1975 | Corsaut | 604/43 |
| 4,482,346 | 11/1984 | Reinicke . | |
| 4,551,128 | 11/1985 | Hakim et al. . | |
| 5,257,971 | 11/1993 | Lord et al. . | |
| 5,320,599 | 6/1994 | Griep et al. | 604/43 |
| 5,453,088 | 9/1995 | Boudewijn et al. | 604/43 |

FOREIGN PATENT DOCUMENTS

WO89/07466  8/1989  WIPO .
WO91/17780  11/1991  WIPO .

*Primary Examiner*—Manuel Mendez
*Attorney, Agent, or Firm*—Hill, Steadman & Simpson

[57] ABSTRACT

In a procedure for flushing a catheter, connected to an apparatus, implanted in a patient for infusing liquid medication, in particular insulin, through the catheter, the infusion channel in the catheter is isolated from the patient and connected in a circuit separated from the patient. Cleaning fluid is then flushed through the circuit. In a device for flushing a catheter according to this procedure, connected to an implanted apparatus for infusing fluid medication, in particular insulin, through the catheter, the catheter is at least of a double-lumen type. One channel is intended for the infusion of the medication through an outlet valve in the catheter, and a second valve is arranged in the tip of the catheter to interconnect the two channels. The second valve is openable, and the outlet valve is closable, either by pressure actuation or by an externally applied signal, so the catheter's two channels are placed in fluid communication to form a circuit, isolated from the patient, for flushing the infusion channel.

22 Claims, 5 Drawing Sheets

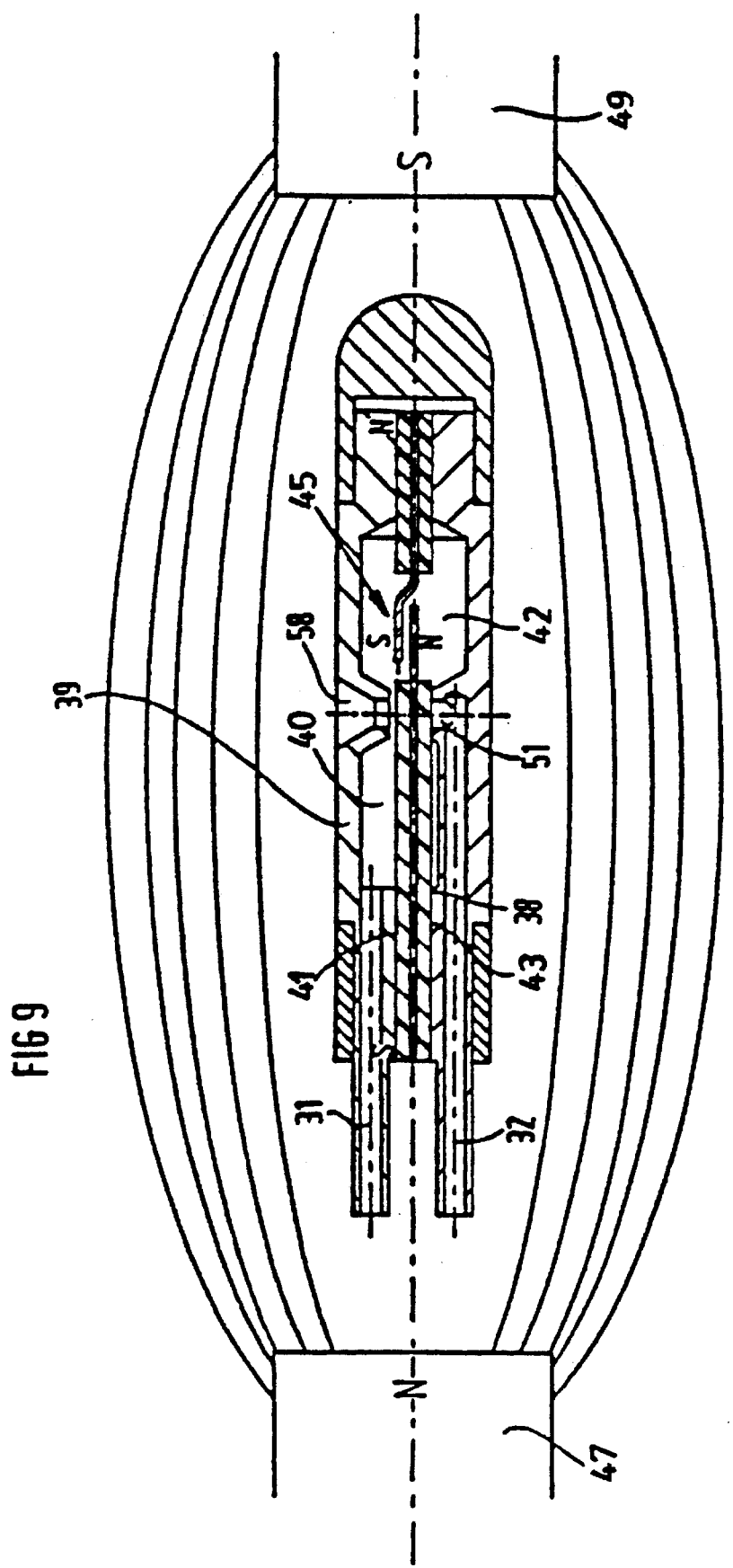

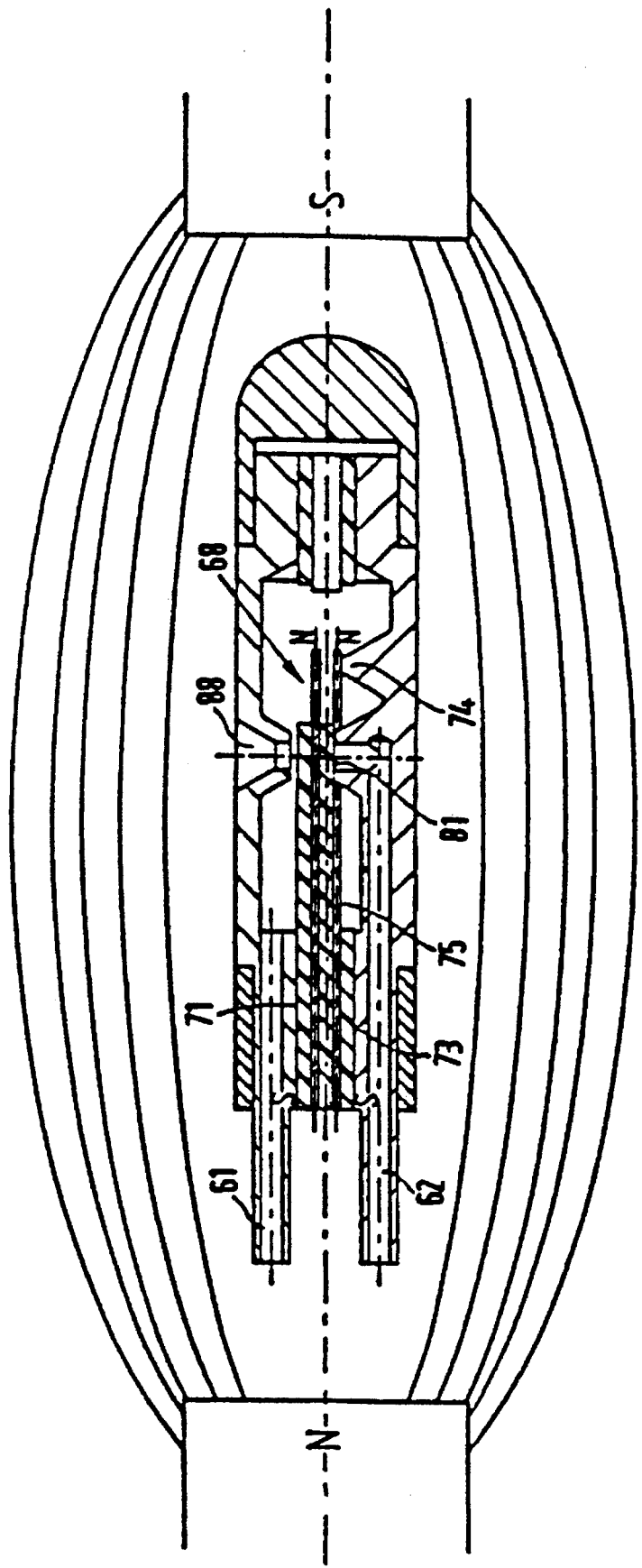

PROCEDURE AND DEVICE FOR FLUSHING A CATHETER

BACKGROUND OF THE INVENTION

1. Field of the Invention

This present invention relates to a procedure and a device for flushing a catheter connected to an apparatus, implanted in a patient, for infusion of liquid medication, in particular insulin, through the catheter.

2. Description of the Prior Art

Blockage of catheters in implanted apparatuses for infusion of liquid medication, e.g., insulin pumps, is a major problem. The blockage is caused by deposition of insulin inside the catheter.

The problem of catheter blockage has hitherto been solved by simply flushing some suitable liquid through the catheter, this flushing liquid and any residual medication ending up in the patient. This procedure has obvious disadvantages. Thus, the choice of flushing liquids is limited. A phenol solution is often employed, but it is not totally clear whether allowing this solution to enter the body is safe. In addition, insulin residue, which can contain altered insulin, enters the patient's body. This could provoke immunity against insulin.

If this flushing is unsuccessful, explantation of the catheter is the only option remaining.

SUMMARY OF THE INVENTION

An object of the present invention is to achieve catheter flushing without flushing liquid coming into contact with patient fluids or tissue, thereby eliminating the aforesaid shortcomings.

The above object is achieved in a procedure for flushing an infusion channel in vivo in a catheter connected to an implanted medication infusion apparatus, wherein the infusion channel is isolated from a patient in whom the catheter is implanted, the infusion channel is then connected to a fluid circuit which is separated from the patient, and the fluid circuit is then flushed with cleaning fluid. After the flushing procedure has been completed, the infusion channel is caused to again be capable of infusing medication to the patient.

In a device constructed in accordance with the principles of the present invention, operating according to the above procedure, the catheter is at least a double-lumen catheter, with one channel forming the infusion channel and having an outlet valve through which medication is infused from the infusion channel into the patient. The other channel of the double-lumen catheter is capable of being placed in fluid communication with the infusion channel by means of a further valve, disposed at a distal end of the catheter. The outlet valve is caused to be closed, and the further valve is caused to be opened so that the infusion channel is in fluid communication with the further channel the two channels forming a fluid circuit which is separated from the patient. Cleaning fluid can then be introduced into this fluid circuit for flushing the infusion channel. After such flushing, the outlet valve and the further valve are returned to their respective normal states so that the two channels are again separated, and the infusion channel is capable of fluid communication with the patient.

Since the catheter's infusion channel in the present invention is isolated from the patient and is connected to a circuit separated from the patient, flushing liquid does not come into contact with the patient's body tissue or fluids, and no deposits in the infusion channel are flushed into the patient's body. Flushing liquids, flows and quantities which are efficient for the cleaning can thus be freely chosen without any risk for the patient, and cleaning residue, e.g. degraded insulin, is discharged outside the patient's body.

According to advantageous embodiments of the invention, the catheter is at least of a double-lumen type, the catheter's two channels being interconnected for flushing at the catheter's end area, forming a closed circuit inside the patient's body with orifices externally accessible via injection needles. The catheter has an outlet valve in the infusion channel, opening to the patient for normal infusion, which is closed prior to flushing.

In a double-lumen catheter, the outlet valve is suitably responsive to the pressures in the infusion and flushing channels, the pressure in the flushing channel being adapted after flushing so the outlet valve is opened by the pressure generated by the medication pumping pump upon a pump stroke. In this way, the outlet valve can be kept closed when the infusion pump is not operating, thereby reducing the risk of deposits etc. forming on the valve's sealing surfaces, with impaired sealing as a result. A closed valve also prevents body fluids from penetrating into the infusion channel.

According to another advantageous version of the procedure according to the invention, the infusion channel is filled after flushing with medication through the flushing channel. The flushing channel is then connected at the catheter tip to a third, purging channel in the catheter. Medication in the flushing channel is then discharged through the, purging channel. The flushing channel is then filled with a gas, suitably air. In this way, a certain measure of elasticity is attained in the flushing channel, and the outlet valve is normally kept closed by a suitable force by adapting the gas pressure to an appropriate value.

According to an advantageous embodiment of the device according to the invention, a distal valve is arranged in the catheter's distal end area for interconnecting the infusion and flushing channels. The outlet valve can be pressure-regulated and closed when the difference between the pressure in the infusion catheter and the pressure in the flushing catheter reaches a first threshold value, and the distal valve can open when the difference between the pressures in the channels attains a second threshold value, which is higher than the first value. This ensures that the outlet valve in the infusion channel closes before the infusion channels are interconnected through the distal valve in the catheter's end area.

According to another advantageous embodiment of the device according to the invention, the outlet valve is a membrane valve, the catheter's channels being connected to spaces in the outlet valve on either side of the membrane. The membrane is spring-biased with a valve spring, preferably a leaf spring, or made of an elastic material and devised so its shape gives the membrane the requisite bias after the membrane is installed in the valve. The magnitude of this spring bias determines the pressure required to open the outlet valve.

According to an alternative version, the valves are extracorporeally magnetically controlled, e.g. with the aid of reed switches.

According to another advantageous embodiment of the catheter according to the invention, a third purging channel, which is connectable to the flushing channel at the tip of the catheter, is provided. After flushing has been concluded, flushing can first be performed with liquid medication until the infusion channel has filled with the medication, whereupon the medication in the flushing channel is flushed out through the purging channel. In this version, the flushing channel can be easily filled with gas so the aforesaid elasticity is achieved in the channel.

In another advantageous embodiment of the device according to the invention, all the surfaces in the outlet valve requiring tight tolerances, such as sealing surfaces between the channels and out to the patient, valve seats etc., are formed in the same plane. This makes simple fabrication and small valve dimensions possible.

According to another advantageous embodiment of the device according to the invention with a multi-lumen catheter, a plurality of outlet valves are connected in series and/or parallel for infusion of several drugs. This permits construction of units of varying sizes and complexity, analogous to e.g. semiconductor and fluidistor technology.

DESCRIPTION OF THE DRAWINGS

FIGS. 9 and 10 respectively show a longitudinal section through the distal end area of a double-lumen catheter in two alternative versions of the device according to the invention shown in FIG. 6.

DESCRIPTION OF THE PREFERRED EMBODIMENTS

Figure 1:
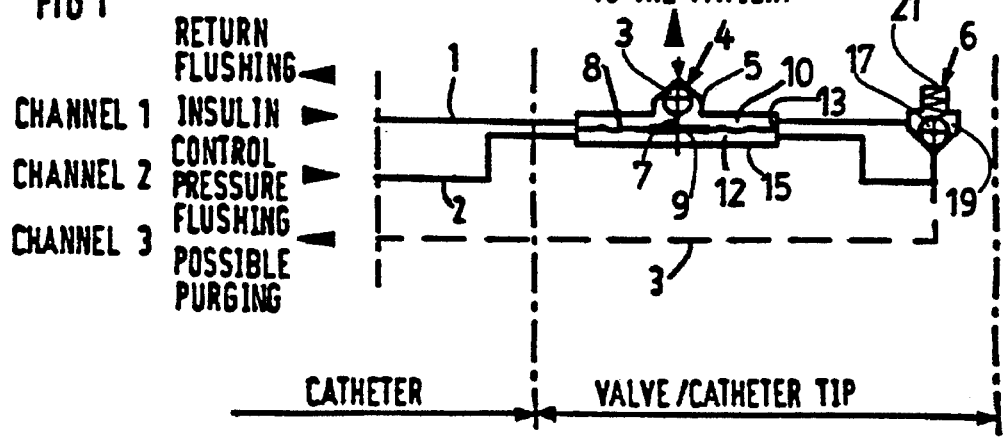
FIG. 1 shows the principle structure of a catheter provided with a flushing device constructed according to the invention in a first embodiment, with a further embodiment shown with dashed lines.

FIG. 1 shows the principle structure of two exemplary embodiments of a catheter equipped with the device according to the invention. The catheter of FIG. 1 is intended for connection to an implanted apparatus for the infusion of a liquid medication, such as insulin. Insulin is supplied in the forward direction through the channel 1, the infusion or insulin channel. The insulin is delivered to the patient through an outlet valve 4 in the channel. The outlet valve 4 is arranged in the catheter's end section. Insulin may become deposited in the insulin channel 1, thereby impeding the flow of insulin from the infusion apparatus pump to the outlet valve 4.

The channel 2 is a flushing and control channel which opens into the channel 1, beyond the outlet valve, as viewed from the infusion apparatus. The flushing channel 2 opens into the insulin channel 1 via a pressure relief valve 6 arranged at the catheter's tip. The pressure relief valve 6 is closed in the normal apparatus operation during delivery of insulin to the patient.

When the insulin channel 1 is to be flushed, flushing liquid is supplied into the flushing channel 2. The pressure relief valve 6 does not then open until the pressure in the flushing channel 2 has reached a specific preset threshold value.

Figure 2:
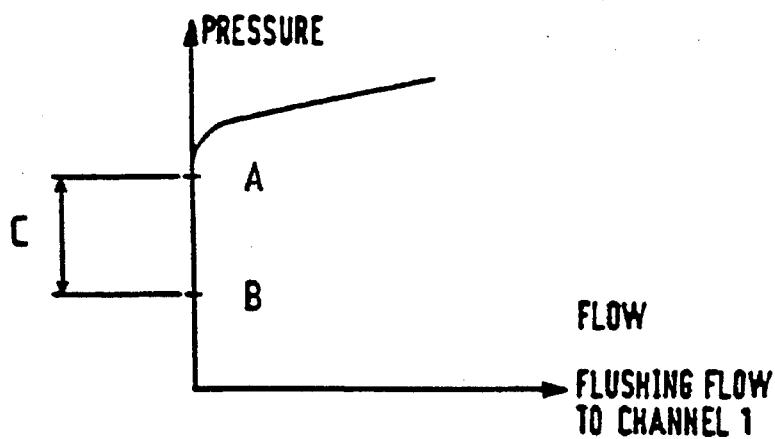
FIGS. 2 and 3 respectively show diagrams of pressure conditions in the flushing channel and in the infusion channel of the catheter shown in FIG. 1.

The outlet valve 4 to the patient is suitably of a membrane type, the flushing channel 2 and the insulin channel 1 being connected to spaces in the outlet valve 4 on either side of the membrane 8. The pressure in the flushing channel 2 and the valve space 12 will act on the membrane 8 so the outlet valve 4 closes to the patient. The preset threshold value for opening the pressure relief valve 6 is selected so the outlet valve 4 is kept reliably closed to the patient before the pressure relief valve 6 opens. This is illustrated in FIG. 2 which shows the relationship between pressure and flow in the flushing channel 2. The lowest closing pressure for the outlet valve 4 is at level B, for example 1.5 bar, and the lowest opening pressure for the pressure relief valve 6 is on level A, for example 2.5 bar. The pressure levels A and B are separated by a safety margin C, as shown in the FIG. 2.

More specifically, the outlet valve 4 contains a ball 3 which is normally seated against a cone-shaped surface 5, so as to close the outlet valve 4. The ball 3 is attached by a pin 7 to a plate 9, which is attached to or forms a part of the membrane 8. The membrane 8 is fixed at locations 11 and 13 to the sidewalls of the chamber 15. The membrane 8, other than the plate 9, consists of elastomeric material which allows the membrane 8 to move upwardly and downwardly (given the orientation shown in FIG. 1) depending on the respective pressures in the spaces 10 and 12, as described below. This movement of the membrane 8 is thus transferred to the ball 3 via the plate 9 and the pin 7, so that the outlet valve 4 is opened and closed by the movement of the membrane 8.

In the relief valve 6, a ball 17 is normally biased against the inner surface of a cone-shaped wall 19 by means of a spring 21. The relief valve 6 is opened as the pressure in the flushing channel 2 increases sufficiently to overcome the bias of the spring 21, i.e., level A in FIG. 2.

When the pressure in the flushing channel 2 reaches level A, the pressure relief valve 6 opens, and flushing liquid flows into the insulin channel 1. The pressure then rises because of the constriction or blockage in the insulin channel 1 which the flushing procedure is intended to remove. This pressure rise acts on the side of the membrane 8 facing the space 10 and counteracts the pressure on the side of the membrane 8 facing the space 12 which serves to ensure closing of the outlet valve 4 to the patient. However, the pressure relief valve 6 closes as soon as the pressure difference drops below the threshold value A and does not re-open until the pressure difference across the pressure relief valve 6 has reached a magnitude corresponding to pressure level A. In flushing, therefore, a pressure difference is ensured across the membrane 8, ensuring that the valve 4 closes to the patient irrespective of the absolute levels of pressure in catheter channels and valves.

Figure 3:
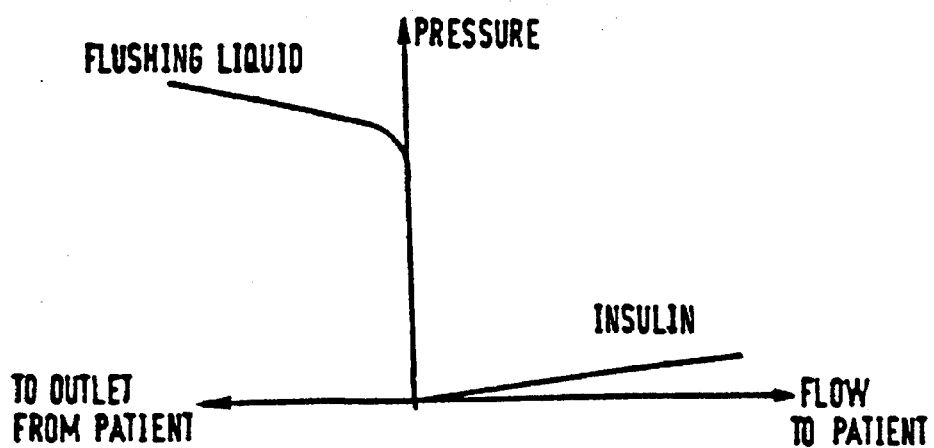

FIG. 3 shows that the delivery of insulin to the patient through the insulin channel 1 in normal operation takes place at a low pressure in the insulin channel 1, whereas retrograde flushing of cleaning fluid through the insulin channel 1 during the flushing procedure takes place at a relatively high pressure.

Since the flushing channel 2 opens into the insulin channel beyond the outlet valve 4, viewed in the direction of insulin flow, the entire insulin delivery part of the catheter becomes accessible for retrograde flushing.

After flushing has been concluded, the pressure on the flushing side of the membrane 8 in the space 12 must be lowered to a level below the infusion device's pumping pressure in order for the outlet valve 4 to open to the patient. This is achieved most simply by sucking a small amount of cleaning fluid back through the flushing channel 2. If the flushing channel 2 is left completely filled with fluid, the outlet valve 4 becomes hydraulically jammed in the position it had when flushing ended.

When the outlet valve 4 is open, there is a risk that the sealing surfaces may become coated with deposits etc., with impaired sealing as a consequence. By providing a certain elasticity in the flushing channel 2, e.g. by the filling of the flushing channel 2 with gas, suitably air, at an appropriate pressure, the gas being allowed to act on the flushing side of the membrane 8, the outlet valve 4 can be kept closed to the patient. The pressure of the air filled on the flushing side of the membrane 8 is selected so this pressure is overcome by the pressure of insulin on the insulin side of the membrane 8 at every pump stroke, and the valve 4 opens. With a closed outlet valve 4, body fluids are prevented from penetrating into the insulin channel 1. Since the area acted on by body fluids at the orifice of the outlet valve 4 is only a fraction of the area on which pressure from the insulin acts, the pressure required for closing the outlet valve 4 can be selected so low that the energy consumed by the infusion pump to open the valve 4 is acceptable. By keeping the valve 4 normally closed in this way, increased security is achieved against insulin leakage due to external decompression. If the pressure in the valve-opening to the patient drops, this drop contributes to the closure of the outlet valve 4. If the valve were not closed or fully sealed, this lower pressure would be propagated to the insulin side of the membrane 8 and reinforce the closure force exerted on the outlet valve 4.

During the flushing procedure, the catheter's channels 1 and 2 are in communication with fluid connections outside the patient by means of injection needles, thereby achieving a closed flushing circuit, separated from the patient.

Conducting the flushing procedure may be simpler, in purely clinical respects, if the channel is provided with a third, purging channel 3, as shown in dashed line in FIG. 1. After flushing has been concluded, insulin can then be added until the insulin channel 1 is completely filled, the insulin in the flushing channel 2 then being removed through the third channel 3.

With the alternative of employing air as an elastic medium, the flushing channel 2 can easily be filled while flushing residue is simultaneously discharged through the third channel 3.

Figure 4:
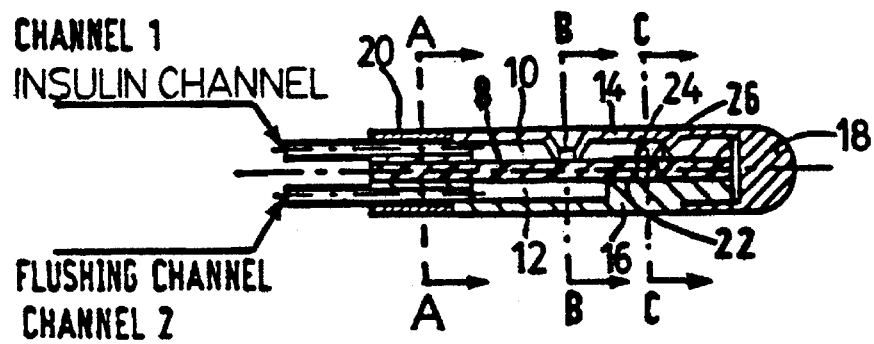
FIG. 4 shows a longitudinal section through the distal end area of a double-lumen catheter with the device of FIG. 1.
Figure 5:
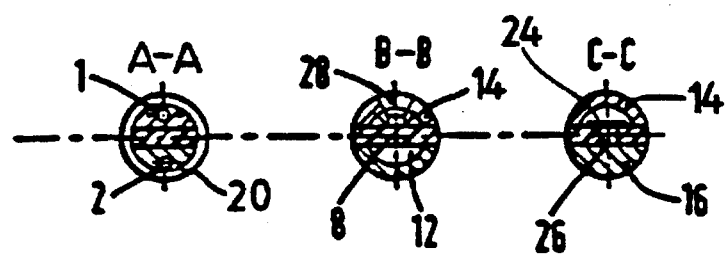
FIGS. 5a, 5b and 5c respectively show cross sections through the catheter in FIG. 4 in three different axial positions.

One example of a practical embodiment of a catheter with the device according to the invention is shown in FIGS. 4 and 5.

With implanted components, keeping dimensions as small as possible is of the utmost importance. Moreover, the valves must be as near to the catheter tip as possible, and rational fabrication of the catheter with the device according to the invention must be possible with a simple design which simultaneously guarantees reliable function.

In the version shown in FIGS. 4 and 5, the pressure relief and outlet valves are arranged in a valve housing which is axially divided into two halves 14 and 16 between which the membrane 8 is stretched: The valve housing halves 14 and 16 are, in turn, clamped together by two circular end pieces 18 and 20.

The membrane 8 is tightly pressed against the part 22 of the valve housing half 16 by a leaf spring 24. When the pressure in the flushing channel 2 and the valve space 12 reaches the preset threshold value for the pressure relief valve, the membrane 8 from the part 22 is pressed so flushing liquid can flow between them and through the hole 26 in the membrane 8 and leaf spring 24, and on to the other side of the membrane 8, past the outlet valve 4, the space 10 and out through the insulin channel 1. As a result of the pressure in the space 12, the membrane 8 is reliably sealed against the end of the conically shaped valve orifice 28 to the patient, and the cleaning fluid is then simultaneously able to flow into the space 10 at the sides of the conically shaped orifice part 28. Thus, the pressure relief valve is formed in this instance from the part of the membrane 8 nearest the tip of the catheter, the part 22 of the valve housing part 16, the hole 26 and the leaf spring 24.

The membrane can be devised for diecasting and the valves may have a "duck-bill" configuration.

In the version shown in FIGS. 4 and 5a, 5b and 5c, the opening pressure for the pressure relief valve is determined by the leaf spring 24. Alternatively, the membrane 8 can be made of a suitable elastic material, such as sheet rubber, and devised so its shape gives the membrane 8 the requisite spring bias (tension) after the membrane has been installed.

The installation of tubing for the respective channels is performed in the conventional way by flanging attachment using heat.

In the embodiments described above both the pressure relief valve 6 and the outlet valve 4 are pressure-regulated. By having the medium to be controlled serve as the carrier of the "control signal," the need for a special control circuit for the valves is eliminated, thereby making a minimal size of the valves possible. In the described versions, the control signals therefore have the form of varying pressures of the cleaning fluid in the flushing channel.

Figure 6:
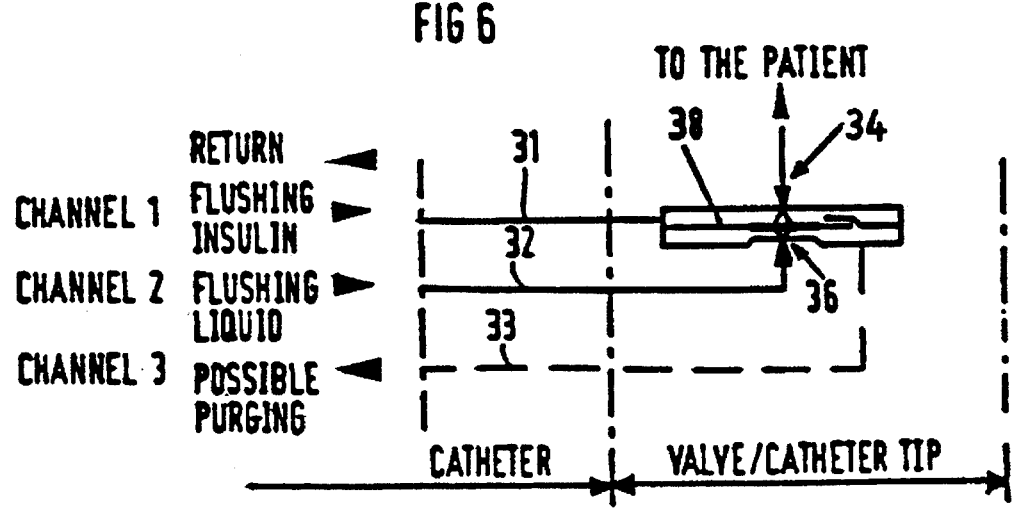
FIG. 6 shows the principle structure of a catheter provided with a flushing device according to the invention in a second embodiment.

FIG. 6 shows the principle structure of alternative versions of the device according to the invention, employing magnetically controlled valves.

The insulin channel 31, flushing channel 32 and purging channel 33 are arranged in a manner analogous the version shown in FIG. 1.

The outlet valve 34 is magnetically controlled and arranged at the outlet to the patient in the same way as in FIG. 1. The pressure relief valve 6 in the version according to FIG. 1 has been replaced by a magnetically controlled flushing valve 36 at the end of the flushing channel 32.

In the version shown in FIG. 9, one end of a soft-iron magnetic reed element 38 is attached inside the valve housing 39. Coatings 41 and 43, made of a material suitable for sealing purposes, are provided on either side of the reed element 38. The read element 38 has a width which is less than the width of the valve space 40, so that a flow of fluid can pass on each side of the read element 38.

One end of a second reed element 45 is attached at the outermost end section of the valve housing 39, with the reed elements 38 and 45 being disposed or bent so the free end of one element is above the free end of the other.

The valve in FIG. 9 operates in the following manner:

When the valve shown in FIG. 9 is in the normal, or inactivated, position, the insulin channel 31 is connected to the valve space 40 and the outlet 58. The orifice 51 of the flushing channel 32 is sealed by the sealing coating 43 on the reed element 38.

As noted above, the free end of the reed element 45 is bent so it, in the inactivated position, overlaps the end section of the reed element 38 and is positioned at a given distance from it.

The valve is activated, as indicated in FIG. 9, by applying a magnetic field across the valve. In practice, this is suitably accomplished by application of a magnet to the outside of the patient's skin at the site of the implanted catheter's tip.

In the case illustrated in FIG. 9, the reed element 38 is magnetized so its south pole S is nearest the external magnet's north pole 47 and thus its north pole N at the opposite, free end. The reed element 45 will have its north pole nearest the external magnet's south pole 49 and, consequently, its south pole S at the opposite, free end.

When the reed elements 38 and 45 are subjected to the externally applied magnetic field, the free end of the moving reed element 38 is drawn to the free end of the fixed reed element 45, thereby opening the orifice 51 of the flushing channel 32 and closing the outlet 58 of the insulin channel 31. This forms a closed path of flow from the flushing channel 32, through the open orifice 51, through the valve spaces 42 and 40 and through the insulin channel 31 for flushing the catheter without the flushing liquid entering the patient's body.

When the external magnetic field is removed, the reed element 38 returns to its normal position, the orifice of flushing channel 32 closes and the orifice 58 of the insulin channel 31 opens to the patient for dosed delivery of medication.

An alternative version of a magnetically controlled valve is shown in FIG. 10 with two reed elements 68 and 75 arranged atop one another and affixed at the same end.

The reed element 68 situated nearest the insulin channel 61 is movable and has a coating 71 and 73 of a material suitable for sealing on both sides, the end sections of the reed elements being left uncoated.

The second reed element 75 presses at its free end against a support and has a hole at the orifice 81 of the flushing channel 62.

In the normal or inactivated valve position, the sealing coating 73 of the reed element 68 presses on the reed element 75, sealing the hole in the latter and, sealing thus, the orifice 81 of the flushing channel 62. The free end sections of the reed elements 68 and 75 overlap one another and are situated at a distance from one another, and the outlet 88 of the insulin channel 61 is open to the patient.

When an external magnetic field is applied in the same way as was described in conjunction with FIG. 9, both the reed elements 68 and 75 are magnetized to an equal degree. In the case illustrated in FIG. 10, both the reed elements 68 and 75 will therefore have north poles N at their free ends which repel each other. The moving reed element 68 will then move away from the second reed element 75, thereby exposing the hole in same and the orifice 81. The outlet 88 is simultaneously closed to the patient by the sealing coating 71, and a closed circuit, isolated from the patient, is achieved through the flushing channel 62, the valve and out through the insulin channel 61 in the same way as in the embodiment for flushing the catheter shown in FIG. 9. When the external magnetic field is removed, the valve then returns to the normal position, shown in FIG. 10, for dosed delivery of medication to the patient.

Magnetization of the reed elements can obviously be reversed, and the design of the free end sections of the reed elements can naturally be varied.

Figure 7:
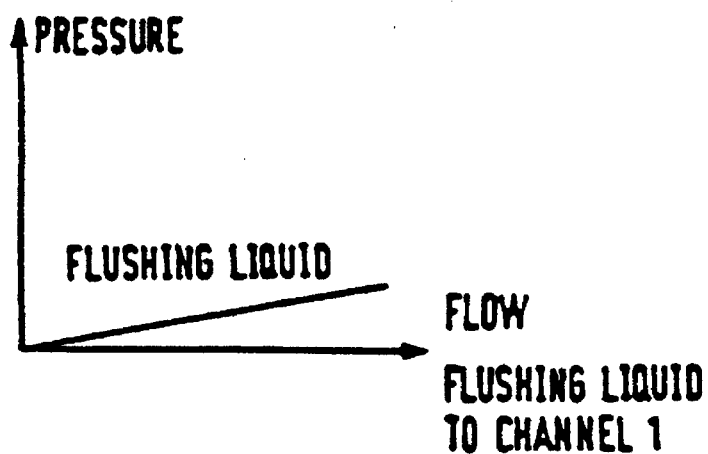
FIGS. 7 and 8 respectively show diagrams of the pressure conditions in the flushing channel and in the infusion channel of the catheter shown in FIG. 6.

FIGS. 2 and 7 illustrate the functional difference between the magnetically controlled valves shown in FIGS. 9 and 10 and the design shown in FIG. 4. In the version shown in FIG. 4, a flushing flow to the insulin channel is not attained until the opening pressure A for the pressure relief valve 6 is achieved (see FIG. 2), whereas a flow starts immediately, at very low pressure, when the orifice of the flushing channel opens in the magnetically controlled cases shown in FIGS. 9 and 10 (see FIG. 7).

Figure 8:
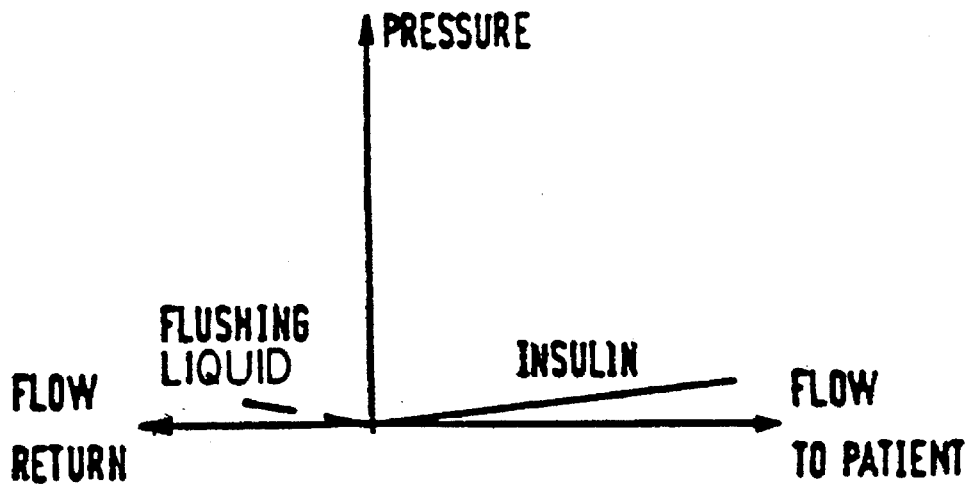

FIG. 8 shows that both the flow of insulin to the patient and retrograde flushing of flushing liquid through the insulin channel occur already at a very low pressure in the magnetically controlled case. Also in the embodiment with the pressure relief valve, a flow of insulin is obtained at low pressure, whereas a flow of flushing liquid is only possible when the pressure exceeds the threshold value for the opening of the pressure relief valve, as is apparent from FIG. 3.

In order to attain rational fabrication, all the surfaces requiring tight tolerances, such as sealing surfaces between the channels and out to the patient, valve seats etc., are formed in the same plane.

The flushing device has been described above as applied to a device for the infusion of insulin, but can naturally be used also for other applications.

If the function of the valves' membrane or the reed elements is considered as a kind of toggle function which, with suitable arrangements, can be made monostable or bistable, a component is achieved which is analogous to pneumatic or hydraulic relays. A plurality of such components can be connected in series or in parallel in different ways to multi-lumen catheters for e.g. infusion of a plurality of different drugs. Such components can obviously be arrayed into different systems for control and regulation.

Although modifications and changes may be suggested by those skilled in the art, it is the intention of the inventor to embody within the patent warranted hereon all changes and modifications as reasonably and properly come within the scope of his contribution to the art.

I claim as my invention:

1. A procedure for in vivo flushing of an infusion channel in a catheter connected to an implanted medication infusion apparatus, said infusion channel normally being in fluid communication with a patient in whom said catheter is implanted, said procedure comprising the steps of:

completely isolating said infusion channel in vivo from fluid communication from said patient in whom said catheter is implanted;

connecting said infusion channel, while isolated, to a fluid circuit separated from said patient; and flushing said fluid circuit with cleaning fluid.

2. The procedure of claim 1 wherein said catheter comprises a double-lumen catheter having a first channel forming said infusion channel, and a second channel and having a distal end, and wherein the step of connecting said infusion channel to a fluid circuit is further defined by interconnecting said first and second channels at said distal end to form said fluid circuit.

3. The procedure of claim 2 wherein said catheter comprises a third, purging channel, and comprising the additional step, after flushing said fluid circuit with cleaning fluid, of filling said infusion channel with medication through said second channel and coupling said second channel to said third channel at said distal end of said catheter for draining medication in said second channel through said purging channel.

4. The procedure of claim 2 wherein said cleaning fluid is flushed in said fluid circuit in a flushing direction, and said procedure comprising the additional step, after flushing said fluid circuit with cleaning fluid, of sucking at least a portion of said cleaning fluid back into said second channel in a direction opposite to said flushing direction for reducing pressure in said second channel.

5. The procedure of claim 4 wherein said infusion channel has a pressure-actuated outlet valve for administering medication from said infusion channel to said patient, and wherein said infusion channel is connectable to a medication pump which operates by generating pressure with a pump stroke, said procedure comprising the additional step, after said pressure is reduced in said second channel, of introducing gas into said second channel at a pressure for causing said outlet valve in said infusion channel to close, and selecting said pressure of said gas in said second channel so that said outlet valve is opened by the pressure generated by a pump stroke of said medication pump.

6. In a catheter having an infusion channel connected to an implanted medication infusion apparatus for infusing liquid medication through said catheter in vivo to a patient, the improvement of a device for in vivo flushing said catheter comprising:

said catheter being at least a double-lumen catheter having a first channel forming said infusion channel, and a second channel and an outlet valve communicating said first channel with said patient;

a further valve disposed at a tip of said catheter openable for interconnecting said first and second channels; and means for closing said outlet valve and opening said further valve for forming a fluid circuit separated from said patient, and means for introducing cleaning fluid into said fluid circuit for flushing said first channel of said catheter.

7. The improvement of claim 6, wherein said cleaning fluid generates a pressure in each of said first and second channels, wherein said outlet valve comprises a pressure-actuated valve which closes when a difference between the pressure in said first channel and the pressure in said second channel reaches a first threshold value and wherein said further valve comprises a pressure-relief valve which opens when said difference reaches a second threshold value which is higher than said first threshold value.

8. The improvement of claim 7 wherein said outlet valve and said pressure relief valve are contained in a common valve housing in an end area of said catheter, said outlet valve and said pressure relief valve being formed by a membrane disposed axially inside said valve housing, said membrane having an inner part for opening and closing an outlet from said first channel to the patient, and having an outer part for opening and closing a connection between said first and second channels.

9. The improvement of claim 8 wherein said outer part of said membrane is biased by a valve spring.

10. The improvement of claim 9 wherein said valve spring comprises a leaf spring.

11. The improvement of claim 7 wherein said outlet valve comprises a membrane valve, and wherein said catheter has first and second spaces on opposite sides of said membrane valve respectively communicating with said first and second channels.

12. A device as claimed in claim 8 wherein said membrane consists of an elastic material and wherein said membrane is mounted in said valve housing for tensioning said elastic material of said membrane.

13. The improvement of claim 6 wherein said outlet valve and said further valve each comprise a magnetically controlled valve.

14. The improvement of claim 13 wherein said outlet valve and said further valve are formed by at least one movable reed element consisting of magnetic material and operable by the application of an external magnetic field.

15. The improvement of claim 14 wherein said movable reed element comprises a reed element movable between a normal position, wherein it closes an orifice between said first and second channels, and an activated position, wherein it closes an outlet of said first channel to said patient and opens said orifice so that said first and second channels are interconnected to form said fluid circuit separated from the patient.

16. The improvement of claim 15 wherein said movable reed element has a free end, and further comprising a fixed reed element having a free end disposed overlapping said free end of said movable reed element and spaced therefrom when said movable reed element is in said normal position, said free ends of said movable and fixed reed elements each being magnetized with opposite polarity when said external magnetic field is applied, said movable reed element being attracted to said fixed reed element in said activated position.

17. The improvement of claim 15 wherein said movable reed element has a free end, and further comprising a fixed reed element having a free end disposed overlapping said free end of said movable reed element and spaced therefrom when said movable reed element is in said normal position, said free ends of said movable and fixed reed elements each being magnetized with the same polarity when said external magnetic field is applied, said movable reed element being repelled from said fixed reed element in said activated position.

18. The improvement of claim 15 wherein said orifice and said outlet are respectively disposed at opposite sides of said movable reed element, and wherein each opposite side of said reed element has a coating thereon for respectively sealing said orifice and said outlet in said normal and activated positions.

19. The improvement of claim 6 wherein said catheter contains a third, purging channel, and means for connecting said purging channel to said second channel at said end of said catheter as part of said fluid circuit.

20. The improvement of claim 6 wherein each of said outlet valve and said further valve has a valve seating surface, and wherein each of said valve seating surfaces are disposed in the same plane.

21. The improvement of claim 6 wherein said catheter comprises a multi-lumen catheter, and contains a plurality of further outlet valves identical to said outlet valve connected in series for infusing a plurality of different medications.

22. The improvement of claim 6 wherein said catheter comprises a multi-lumen catheter, and contains a plurality of further outlet valves identical to said outlet valve connected in parallel for infusing a plurality of different medications.

* * * * *